(12) United States Patent
Davis-Sproul et al.

(10) Patent No.: US 6,387,367 B1
(45) Date of Patent: May 14, 2002

(54) HUMAN MESENCHYMAL STEM CELLS

(75) Inventors: Janice M. Davis-Sproul, Towson; Mark Aaron Moorman; Renee Marie McNeil, both of Baltimore; Donald William Simonetti, Jr., Forest Hill; Lora Catherine Hammill, Bel Air; Stewart Craig, Timonium, all of MD (US)

(73) Assignee: Osiris Therapeutics, Inc., Baltimore, MD (US)

( * ) Notice: Subject to any disclaimer, the term of this patent is extended or adjusted under 35 U.S.C. 154(b) by 0 days.

(21) Appl. No.: 09/321,924

(22) Filed: May 28, 1999

Related U.S. Application Data (60) Provisional application No. 60/087,123, filed on May 29, 1998.

(51) Int. Cl.⁷ .................... A01N 43/04; A01N 63/00; A61K 48/00; C12N 15/00; C07K 16/00
(52) U.S. Cl. .............. 424/93.1; 514/44; 424/93.21; 424/93.2; 435/320.1; 435/7.1; 530/387.1
(58) Field of Search ................ 424/93.21, 93.1, 424/93.2; 435/320.1, 325, 7.1; 514/44; 530/387.1; 536/23.1, 23.5

(56) References Cited

U.S. PATENT DOCUMENTS 5,486,359 A * 1/1996 Caplan et al. ............. 424/93.7
5,591,625 A * 1/1997 Gerson et al. ........... 435/240.2
5,736,396 A * 4/1998 Bruder et al. ............... 435/366

OTHER PUBLICATIONS

Moorman et al. Phenotypic and functional characterization of the pluripotent human mesenchymal stem cell throughout extended passage culture. Blood, 90/10, Suppl. 1 Pt. 2, 344 B, 1997.*

Koc et al. Culture–expanded autologous human mesenchymal stem cells circulate in blood and retain proliferative capacity following iv infusion into breast cancer patients. Blood, 90/10, Suppl 1 Pt. 1. 367A, 1997.*

Mackay et al. Human mesenchymal stem cells in vitro produce an extracellular matrix resembling immature cartilage. Molecular Biology of the Cell, 8 Suppl, 71 A, 1997.*

Hubbell et al. Tissue engineering. C & EN, pp. 42–54, 1995.* van den Bos et al. Human mesenchymal stem cells respond to fibroblast growth factors. Human Cell, vol. 10, No. 1, pp. 45–50, 1997.*

* cited by examiner

*Primary Examiner*—Scott D. Priebe
*Assistant Examiner*—Eleanor Sorbello
(74) *Attorney, Agent, or Firm*—Elliot M. Olstein; Raymond J. Lillie (57) ABSTRACT

Human mesenchymal stem cells having the phenotype SH3+, CD45+ can be isolated. These precursor mesenchymal item cells are useful for treatment of patients in need of mensenchymal stem cell.

22 Claims, 2 Drawing Sheets

FIG. 1A pre-fractionation

FIG. 1B

SH3 negative fraction

FIG. 1C

SH3 positive fraction

FIG. 2

HUMAN MESENCHYMAL STEM CELLS

This application is based on U.S. provisional application Ser. No. 60/087,123 filed May 29, 1998.

BACKGROUND OF THE INVENTION

Mesenchymal stem cells (MSCs) are the formative pluripotential blast cells found inter alia in bone marrow, blood, dermis and periosteum that are capable of differentiating into more than one specific type of mesenchymal or connective tissue (i.e. the tissues of the body that support the specialized elements; e.g. adipose, osseous, stroma, cartilaginous, elastic and fibrous connective tissues) depending upon various influences from bioactive factors, such as cytokines. The potential to differentiate into cells such as osteoblasts and chondrocytes is retained after isolation and expansion in culture; differentiation occurs when the cells are induced in vitro under specific conditions or placed in vivo at the site of damaged tissue.

Epitopes on the surface of the human mesenchymal stem cells (hMSCs) are reactive with certain monoclonal antibodies known as SH2, SH3 and SH4 described in U.S. Pat. No. 5,486,359. These antibodies can be used as reagents to screen and capture the mesenchymal stem cell population from a heterogeneous cell population, such as exists, for example, in bone marrow.

Hematopoietic stem cells (HSCs) are the formative pluripotential blast cells found inter alia in bone marrow and peripheral blood that are capable of differentiating into any of the specific types of hematopoietic or blood cells, such as erytlirocytes, lymphocytes, macrophages and megakaryocytes. The expression of a particular antigen or antigens on the cell surface or in the cytoplasm and the intensity of expression indicate the stage of maturation and lineage commitment of the hematopoietic stem cell. Human hematopoietic stem cells (hHSCs) are reactive with certain monoclonal antibodies, such as CD34, recognized as being specific for hematopoietic cells.

Thus, human hematopoietic stem cells and human mesenchymal stem cells have been readily distinguishable by their immunospecific profiles.

SUMMARY OF THE INVENTION

The present invention provides a population of human mesenchymal stem cells enhanced in cells that are positive for CD45 antibody markers. As hereinafter indicated, a mesenchymal stem cell is one which is capable of differentiating into more than one specific type of mesenchymal tissue cell. Applicants have provided a population of precursor mesenchymal stem cells ("pre-MSCs") which is positive for CD45. These precursor mesenchymal stem cells can differentiate into the various mesenchymal lineages, for example, the chondrocyte, adipocyte and osteoblast lineages.

In another aspect, the present invention provides a population of human mesenchymal stem cells that are CD45 positive and positive for at least one of the SH2, SH3 or SH4 markers. The mesenchymal stem cells of the present invention are preferably positive for at least the SH3 marker. In another aspect, the precursor mesenchymal stem cells are positive for the SH2 marker.

These precursor mesenchymal stem cells may be obtained using antibodies to markers of mesenchymal and hematopoietic cells. Unexpectedly, it was found that a significant number of cells positive for select markers of mesenchymal stem cells were further characterized as being CD45 positive. CD45 is a marker commonly found on leukocytes and hematopoietic cells and not on cultured mesenchymal stem cells. Although not intending to be bound by any theory, it is believed that the population of cells of the present invention comprises a precursor cell to more mature, though not committed, mesenchymal stem cells.

The invention further provides a method for recovering an isolated population of CD45+ human mesenchymal stem cells from bone marrow or other mesenchymal stem cell source of an individual by (i) obtaining bone marrow tissue or other tissue source of mesenchymal stem cells from a donor; (ii) isolating a population of cells enriched in mesenchymal stem cells therefrom; and (iii) further selecting CD45+ cells from the population of human mesenchymal stem cells to obtain a population of mesenchymal stem cells that are enriched in CD45+ mesenchymal stem cells.

In a further aspect, the invention provides a method for recovering an isolated population of CD45+ human mesenchymal stem cells that are also positive for at least one of SH2, SH3 or SH4 markers from bone marrow or other mesenchymal stem cell source of an individual by (i) obtaining bone marrow tissue or other source of mesenchymal stem cell from a donor (ii) isolating a population of cells enriched in mesenchymal stem cells therefrom; (iii) selecting from the cell population a population of mesenchymal stem cells that are positive for at least one of SH2, SH3 or SH4 markers; and (iv) further selecting CD45+ cells from the population of human mesenchymal stem cells of step (iii) to obtain a population of mesenchymal stem cells that are positive for at least one of either SH2, SH3 or SH4 markers and CD45+. In a preferred embodiment, the CD45 cell population is at least SH3 positive.

BRIEF DESCRIPTION OF THE DRAWINGS

FIG. 1 shows FACScan histograms for the expression of CD45 cell surface antigens on the three fractions of human mesenchymal stem cells FIG. 1A prefractionation.

DETAILED DESCRIPTION OF THE INVENTION

The present invention involves the isolation and enhancement of a subset population of human mesenchymal stem cells. In one embodiment, the present invention provides a population of cells having an SH3+/CD45+ phenotype and which are believed to be a precursor mesenchymal stem cell. The human mesenchymal stem cell population of the present invention is capable of differentiation into the chondrocytic, adipocytic and osteoblast cell lineages.

The mesenchymal stem cells of the present invention can be isolated from peripheral blood or bone marrow. "Isolated" as used herein signifies that the cells are placed into conditions other than their natural environment. The term "isolated" does not preclude the later use of these cells thereafter in combinations or mixtures with other cells. A method of preparing human marrow mesenchymal stem cell cultures has been described in U.S. Pat. No. 5,486,359. Several techniques are known to those of skill in the art for the rapid isolation of mesenchymal stem cells. Approaches to mesenchymal stem cell isolation include leucopheresis, density gradient fractionation, immunoselection and differential adhesion separation.

The cells of the present invention are maintained in culture media which can be a chemically defined serum free media or can be a "complete medium", such as Dulbecco's Modified Eagles Medium Supplemented with 10% serum (DMEM). Suitable chemically defined serum free media are described in U.S. Ser. No. 08/464,599 and WO96/39487, and "complete media" are described in U.S. Pat. No. 5,486,359. Chemically Defined Medium comprises a minimum essential medium such as Iscove's Modified Dulbecco's Medium (IMDM) (Gibco), supplemented with human serum albumin, human Ex Cyte lipoprotein, transfernin, insuin, vitamins, essential and non essential amino acids, sodium pyruvate, glutainine and a mitogen. These media stimulate mesenchymal stem cell growth without differentiation.

The mesenchymal stem cells of the present invention isolated from peripheral blood or bone marrow may further be culture-expanded. The cells may be expanded, before or after freezing thereof The media described herein are also suitable for the culture expansion of the mesenchymal stem cells.

The isolated mesenchymal stem cells of the present invention may further be purified. In a preferred embodiment, "purified" indicates that the cell population contains less than 5% impurities, impurities being for example, cells that are not CD45+. The purified cell population can later be used in combinations or mixtures as is appropriate.

The present invention contemplates any suitable method of employing monoclonal antibodies to separate mesenchymal stem cells from other cells, e.g., recovered from bone marrow. Accordingly, included in the present invention is a method of producing a population of mesenchymal stem cells comprising the steps of providing a cell suspension of tissue containing mesenchymal stem cells; contacting the cell suspension with one or a combination of monoclonal antibodies which recognize an epitope on the mesenchymal stem cells; and separating and recovering from the cell suspension the cells bound by the monoclonal antibodies. The monoclonal antibodies may be linked to a solid-phase and utilized to capture mesenchymal stem cells from tissue samples. The bound cells may then be separated from the solid phase by known methods depending on the nature of the antibody and solid phase.

Monoclonal based systems appropriate for preparing the desired cell population include magnetic bead/paramagnetic particle column utilizing antibodies for either positive or negative selection; separation based on biotin or streptavidin affinity; and high speed flow cytometric sorting of immunofluorescent-stained mesenchymal stem cells mixed in a suspension of other cells. Thus, the method of the present invention includes the isolation of a population of hMSCs and enhancement using monoclonal antibodies raised against surface antigens expressed by marrow-derived hMSCs, i.e. SH2, SH3 or SH4. Deposits of the cell line cultures identified as SH2, SH3 and SH4 are on deposit with the American Type Culture Collection, 10801 University Blvd. Manassas, Va. 20110-2209, and are assigned the ATCC accession numbers HB 10743, BH 10744 and HB 10745, respectively. These monoclonal antibodies provide effective probes which can be utilized for identifying, quantifying, and purifying mesenchymal stem cells, regardless of their source in the body.

In one embodiment, the isolation of the cell population of the present invention may comprise utilizing a combination of one or more antibodies that recognize a known marker on mesenchymal stem cells as well as an antibody which recognizes CD45. One method for such preparation of the precursor cells of the present invention is to first select a population of cells expressing a marker identifying mesenchymal stem cells, for example, SH3 or SH2 by immunomagnetic selection of a low density human bone marrow cell sample. Alternatively, it is contemplated that the initial cell selection can be based on the CD45 marker and the cell population be further characterized using the hMSC monoclonal antibodies.

In another embodiment, it is contemplated that a cell population can be selected based on the CD14 marker. CD14 is a membrane protein that functions as a receptor for endotoxin (lipopolysaccharide, LPS) and is expressed strongly on the surface of monocytes, but not expressed by myeloid progenitors.

Thus, in one aspect, in certain embodiments described herein, the mesenchymal stem cell population Population 1 (Pop 1) is identified by FACS by the relative brightness of immunofluorescent stained antibodies bound thereto as SH2 and SH3 bright/CD45 dim/CD14 dim. In comparison, SH2 and SH3 are present on culture expanded MSCs; CD45 is absent on culture expanded MSCs; and CD14 is absent on culture expanded MSCs.

In a still further aspect of the invention, a cell population can be selected based on a fibroblast cell surface marker, for example the antifibroblast antibody found on Miltenyi anti-fibroblastiicrobeads (Miltenyi catalog # 506-01).

It is further contemplated that the hereinabove described methods may be applied to a population of culture-expanded mesenchymal stem cells such that cells having a Pop 1 phenotype may be isolated from the population of culture-expanded mesenchymal stem cells.

The present invention is directed to various methods of utilizing the CD45+ human mesenchymal stem cells of the present invention for therapeutic and/or diagnostic purposes. These uses include regenerating mesenchymal tissues which have been damaged through acute injury, abnormal genetic expression or acquired disease; treating a host having damaged mesenchymal tissue by removal of small aliquots of bone marrow, isolation of their mesenchymal stem cells and treatment of damaged tissue with the CD45+ hMSCs combined with a suitable biocompatible carrier material for delivering the MSCs to the damaged tissue sites; producing various mesenchymal tissues; detecting and evaluating growth factors or inhibitory factors relevant to MSC self-regeneration and differentiation into committed mesenchymal lineages; and developing mesenchymal cell lineages and assaying for factors with mesenchymal tissue development.

The hMSCs of the present invention -may be used in a variety of ways. For example, the hMSCs can be employed as part of cell replacement therapy. Specifically, the hMSCs can be infused alone or added to bone marrow cells for bone marrow transplant procedures. Other applications also particularly contemplated are orthopedic, are such as augmentation of bone formation. Other applications include, for example, the treatment of osteoartbritis, osteoporosis, traumatic or pathological conditions involving any of the connective tissues, such as a bone defects, connective tissue defects, skeletal defects or cartilage defects. It is also contemplated that exogenous genetic material can be introduced into the cells while ex vivo, and that the cells be read ministered for production of exogenous proteins in vivo. Genetic modification of mesenchymal stem cells is discussed more fully in U.S. Pat. No. 5,591,625.

The present invention is not limited to a specific method for recovering the cells. For example, such cells may be isolated by procedures which do not use antibodies, provided that the cells are positive for CD45 and are positive for at least one of SH2, SH3 or SH4, preferably at least SH3, and are capable of differentiating into one or more than one mesenchymal cell lineage, and preferably into most, if not all, of the mesenchymal cell lineages. In a particularly preferred embodiment, the cells are also capable of self renewal. Thus, a human mesenchymal stem cell which is SH3+ and CD45+ in accordance with the invention may be recovered by techniques other than the use of SH3+ and CD45+ antibodies. Thus, the term "human mesenchymal stem cell which is SH3+ and CD45+" means a stem cell that has both markers and is capable of differentiating into more than one mesenchymal stem cell lineage.

The following examples are provided to further illustrate and describe the present invention; however, the scope of the present invention is not intended to be limited thereby.

EXAMPLE 1

Isolation of hMSCs from Human Bone Marrow

Bone marrow aspirates were obtained from three volunteers, donors 271, 281 and 332. Density centrifugation of the bone marrow aspirates was performed using Activated Cell Therapy (ACT) Bouyant Density solution (1.0720 g/ml) in conical tubes (Dendreon, Mountain View Calif.) and cells were isolated from the light density fraction. Cells were washed and resuspended in Dulbecco's PBS at a concentration of $2 \times 10^7$ cells/ml. The cells were incubated with blocking antibody (human IgG 1 mg/ml in PBS azide-free) for 10 minutes at 4° C. with rotation followed by a 30 minute incubation at 4° C. with 1 ug/1×107 cells SH3 antibody. Cell from donors 1 and 2 were washed twice with PBS/0.5%BSA and resuspended in PBS to $2 \times 10^7$ cells/ml. Dynal beads (washed 3 times with PBS) were added and the suspension was mixed for 30 minutes at 4° C. Bound cells were magnetically separated from unbound cells. Cells from donor 332 were washed 2× with Miltenyi buffer and incubated for 20 minutes at 4° C. with mixing with rat anti-mouse IgG2 beads (1 ml of microbeads per $5 \times 10^8$ cells) (50 nm Miltenyi Biotec, Auburn, Calif.) and selected according to manufacturer's instructions.

Three cell populations from each donor were analyzed: the start fraction (light density unseparated cells), SH3 selected cells (cells attached to the derivatized magnetic beads) and SH3 unselected cells (cells that did not attach to the derivatized beads). The hematopoietic and mesenchymal stem cell contents of the three samples were assayed as described below.

Cell Numbers. Cell numbers contained in the fractions are shown in Table 1. The SH3 selected fractions contained 4.2, 4.8, and 6.2% of the starting cells. The SH3 unselected fractions yielded 88, 70, and 87% of the starting cells.

TABLE 1

Cell Numbers (yields)

| Fraction | Total cells (x10⁶) | % Cell Recovery | % Viability |
|---|---|---|---|
| Donor 271 | | | |
| Start | 262 | | |
| SH3 selected | 11 | 4.2 | 94.2 |
| SH3 unselected | 231 | 88.1 | 92.8 |

TABLE 1-continued

Cell Numbers (yields)

| Fraction | Total cells (x10⁶) | % Cell Recovery | % Viability |
|---|---|---|---|
| Donor 231 | | | |
| Start | 217 | | |
| SH3 selected | 10.5 | 4.8 | 90.0 |
| SH3 unselected | 150 | 70.0 | 99.5 |
| Donor 332 | | | |
| Start | 207 | | |
| SH3 Selected | 12.8 | 6.2 | |
| SH3 Unselected | 181 | 87.4 | |

Colony forming Unit F Assay. The CFU-F assay measures colonies grown in complete culture media. Nucleated cells were suspended in hMSC medium to a concentration of $2 \times 10^6$ cells in 40 mls, and were plated in 100 mm tissue culture dishes at $5 \times 10^5$ cells per plate. After 14 days cells were fixed with glutaraldehyde and stained with crystal violet. The results are shown in Table 2.

TABLE 2

CFU-F Assay

| Fraction | # CFU-F colonies/ $5 \times 10^4$ cells | Total CFU-F (% of total) |
|---|---|---|
| Donor 271 | | |
| Start | Not done | |
| SH3 selected | 15 | $3.3 \times 10^3$ |
| SH3 unselected | 0 | 0 |
| Donor 281 | | |
| Start | 1.3 | $5.77 \times 10^3$ |
| SH3 selected | 16.7 | $3.50 \times 10^3$ (61%) |
| SH3 unselected | 0.7 | $2.01 \times 10^3$ (35%) |
| Donor 332 | | |
| Start | 5.7 | $2.36 \times 10^4$ |
| SH3 Selected | TNTC | |
| SH3 Unselected | 0 | 0 |

TNTC = too numerous to count

The SH3 selected fraction showed enrichment for colonies when compared to the starting cell sample; in fact, the Miltenyi selected fraction (donor 332) had too many colonies to count. In the SH3 unselected fraction one of 3 CFU-F assays had only 0.7 colonies per 50,000 cells plated, while the remaining 2 cultures had no colony growth.

TABLE 3

Hematopoietic progenitor cells Total Colonies (% Recovery)

| Fraction | BFU-E | CFU-GM | CFU-GEMM |
|---|---|---|---|
| Donor 271 | | | |
| Start | $5.61 \times 10^5$ | $5.30 \times 10^5$ | 0 |
| SH3 selected | 0 | $2.45 \times 10^2$ (0.05%) | 0 |
| SH3 unselected | $3.82 \times 10^5$ (68%) | $4.72 \times 10^5$ (89%) | 0 |
| Donor 281 | | | |
| Start | $4.63 \times 10^5$ | $2.62 \times 10^5$ | 0 |
| SH3 selected | $1.16 \times 10^2$ (0.02%) | $1.16 \times 10^2$ (0.04%) | 0 |
| SH3 unselected | $3.08 \times 10^5$ (67%) | $2.56 \times 10^5$ (98%) | 0 |

TABLE 3-continued

Hematopoietic progenitor cells Total Colonies (% Recovery)

| Fraction | BFU-E | CFU-GM | CFU-GEMM |
|---|---|---|---|
| Donor 332 | | | |
| Start | $6.07 \times 10^5$ | $4.28 \times 10^5$ | $8.28 \times 10^4$ |
| SH3 Selected | 0 | $1.28 \times 10^3$ (0.3%) | 0 |
| SH3 Unselected | $5.61 \times 10^5$ (92%) | $4.40 \times 10^5$ (103%) | $6.03 \times 10^4$ (73%) |

The SH3 unselected fractions contained 89, 98, and 103% of the starting hematopoietic CFU-GM colonies (Table 3). Only 0.04, 0.05, and 0.3% of the starting CFU-GMs were found in the SH3 selected cell fraction (Table 3).

Mesenchymal stem cell culture. $3.2 \times 10^6$ cells of Donors 271 and 281 were added into 2 wells of a 6 well plate. The cells were harvested after 13 days in culture. The results are shown in Table 4.

For sample donor 332 each well was seeded with $0.8 \times 10^6$ cells. On Day 11, based on microscopic examination, two of four SH3 selected cell wells were harvested. All other wells were harvested after 14 days in culture. Results are shown in Table 5.

The results of the MSC cultures showed that the SH3 selected cells expanded with the same or greater efficiency than the starting cell fraction and the harvested cells had the distinctive MSC morphology and phenotype. In MSC complete culture medium after primary culture the cell yield from this SH3 unselected fraction was low (1.3, 3.8, & 1.6%) compared to the starting cell fractions (17.5, 19.4, & 44.5%, respectively).

TABLE 4

Cell numbers P0 Culture & Harvest

| Fraction | Total cells harvested | % Yield |
|---|---|---|
| Donor 271 | | |
| Start | $5.6 \times 10^5$ | 17.5% |
| SH3 selected | $5.7 \times 10^5$ | 17.8% |
| SH3 unselected | $0.42 \times 10^5$ | 1.3% |
| Donor 281 | | |
| Start | $6.2 \times 10^5$ | 19.4% |
| SH3 selected | $6.3 \times 10^5$ | 19.7% |
| SH3 unselected | $1.2 \times 10^5$ | 3.8% |

TABLE 5

Donor 332

| Fraction | Number of Cells harvested per well | Yield (% of cells seeded) | Appearance |
|---|---|---|---|
| Start | $3.56 \times 10^5$ | 44.5 | 85% confluent |
| SH3 Selected (Day 11) | $3.00 \times 10^5$ | 37.0 | 85% confluent |
| SH3 Selected (Day 14) | $5.50 \times 10^5$ | 68.8 | 100% confluent |
| SH3 Unselected | $1.30 \times 10^4$ | 1.6 | no spindle shaped cells; cigar shaped or round cells |

Cells from the donors 271 and 281 were continued in culture and Passage 1 cells were collected and examined by flow cytometry; the cells were MSCs by morphology and phenotype.

Visual observation of these cultures during P0 showed that MSC-like colonies also contained cells with magnetic beads attached. The cells were replated in flasks or wells depending on the total cells available. The cells were harvested after 8 days in culture.

TABLE 6

Cell Numbers P1 Culture & Harvest

| Fraction | # Cells Plated | # Cells Harvested | Fold Increase |
|---|---|---|---|
| Donor 271 | | | |
| Start | $4.3 \times 10^5$ | $2.6 \times 10^6$ | 6.0 |
| SH3 selected | $4.3 \times 10^5$ | $1.8 \times 10^6$ | 4.2 |
| SH3 unselected | $4.2 \times 10^4$ | $0.13 \times 10^6$ | 3.1 |
| Donor 281 | | | |
| Start | $4.3 \times 10^5$ | $2.3 \times 10^6$ | 5.3 |
| SH3 selected | $4.3 \times 10^5$ | $2.0 \times 10^6$ | 4.5 |
| SH3 unselected | $1.2 \times 10^5$ | $0.26 \times 10^6$ | 2.3 |

The cultured cells from the SH3 selected Day 11 harvest were analyzed. The cells were SH2+, SH3+, SH4+ and CD45−, corresponding to a mature cultured mesenchymal stem cell phenotype.

Figure 1A:
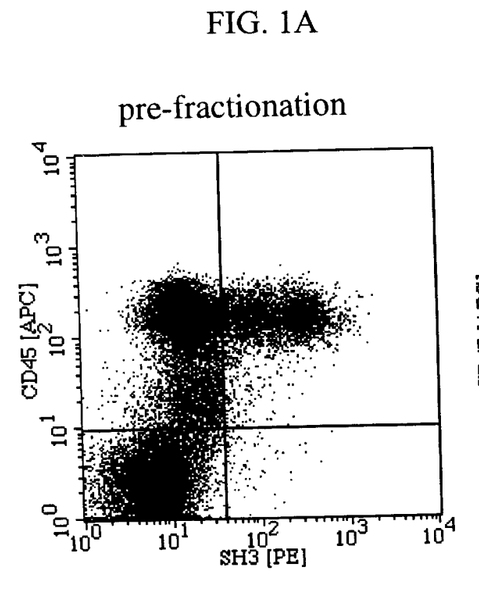
Figure 1B:
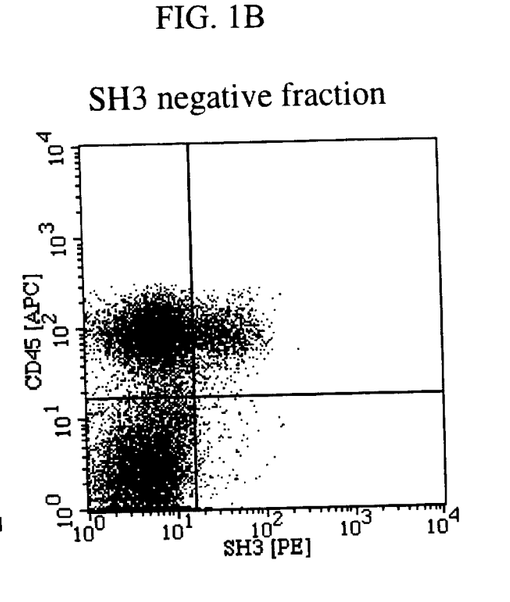
FIG. 1B SH3 selection negative fraction.
Figure 1C:
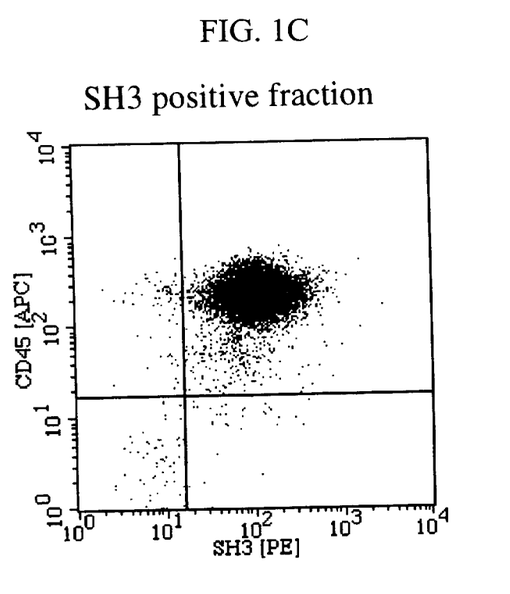
FIG. 1C SH3 selection positive fraction.

Flow Cytometry Analysis. The cell fractions of Donor 332 were analyzed using SH3 and CD45 antigen markers. FIG. 1 shows the FACS histogram of the CD45 analysis.

TABLE 7a

Flow Analysis Donor 332

| Fraction | Total cells | % SH3+ | Total SH3+ cells | Yield (%) |
|---|---|---|---|---|
| Start | $207 \times 10^6$ | 20.8 | $43.0 \times 10^6$ | |
| SH3 Selected | $12.8 \times 10^6$ | 98.8 | $12.6 \times 10^6$ | 29.4 |
| SH3 Unselected | $181 \times 10^6$ | 13.6 | $24.6 \times 10^6$ | 57.2 |

TABLE 7b

| Fraction | Total cells | % SH3+/CD45+ | Total SH3+/CD45+ Cells | Yield (%) |
|---|---|---|---|---|
| Start | $207 \times 10^6$ | 20.4 | $42.2 \times 10^6$ | |
| SH3 Selected | $12.8 \times 10^6$ | 98.4 | $12.6 \times 10^6$ | 29.8 |
| SH3 Unselected | $181 \times 10^6$ | 12.3 | $22.3 \times 10^6$ | 52.8 |

The results in Tables 7a and b of the flow analysis of the donor 332 sample demonstrated a SH3 purity of 98.8% with greater than 99.5% of these cells being CD45+. The total number of CD45-cells in the sample was 0.42%.

The results indicated that the precursor to the mesenchymal stem cell observed in culture was SH3 positive and CD45 positive and this cell can be isolated using SH3 antibody in conjunction with immunomagnetic beads or other immunoselection methods.

EXAMPLE 2

MSC Isolation using SH2 Cell Selection

Biotin-anti-SH2 antibody and rat anti-mouse IgG1 magnetic microbeads were used to isolate two fractions of cells from light-density bone marrow cells: SH2 bound and SH2 unbound. These cell fractions were placed into standard MSC culture conditions to determine the MSC proliferative potential of the cell population contained in these fractions.

Anti-IgG1 microbeads were from Miltenyi Lot # NE7200. VS Column was from Miltenyi Lot #0231). Pre-separation filters were 30 um from Miltenyi Lot #55. Miltenyi buffer: phosphate buffered saline pH 7.2 supplemented with 0.5% BSA and 2 mM EDTA. Flow staining was performed using the manufacturer's suggested instructions. Flow analysis was performed using either the FACS Calibur or the FACS Vantage. Cell viability and cell number were determined using trypan blue.

Light density cells were isolated from a human bone marrow aspirate (donor #426) using Dendreon (Seattle, Wash.) solution BDS72 following density centrifugation of bone marrow aspirates. Aliquots were removed as controls for flow analysis and cell culture. The remaining cells were diluted to a cell count of $2 \times 10^7$ cells/ml using Miltenyi buffer. Cells were incubated with IgG at 40 ul per ml of cell suspension for 10 minutes at 4° C. with mixing. Cells were centrifuged for 10 minutes at 1000 RPM. The cell pellet was incubated with the anti-SH2 antibody at 10 ug per $1 \times 10^7$ cells for 30 minutes at 4° C. with mixing. The cells were washed twice with cold buffer. The cell pellet was resuspended in Miltenyi buffer (80 ul of buffer per $10^7$ cells). Anti-IgG1 microbeads were added (20 ul of beads per $10^7$ cells). The mixture was incubated at 4° C. for 15 minutes with mixing. Miltenyi buffer was added to dilute the mixture and wash the cells. The cells were centrifuged for 10 minutes at 1000 RPM. The cell pellet was resuspended in Miltenyi buffer (0.5 ml of buffer $10^8$ per cells). The VS column was primed following the manufacturer's instructions. The pre-filter was primed following the manufacturer's instructions. The cell/microbead suspension was added to the pre-filter and the suspension drained through the column. The effluent was collected as the 'SH2 unbound' fraction. The column was rinsed twice with 3 ml of Miltenyi buffer and this effluent was added to the 'SH2 unbound' fraction. The column was removed from the magnet and placed over a tube labeled 'SH2 bound'. Five ml of Miltenyi buffer was added to the column and a syringe plunger used to push the cells into the tube. A fresh column was primed and the cells in the 'SH2 bound' tube were added to the second column. The cell/microbead suspension was added to the pre-filter and the suspension drained through the column. The effluent was collected as the 'SH2 unbound' fraction. The column was rinsed twice with 3 ml of Miltenyi buffer and this effluent was added to the 'SH2 unbound' fraction. The column was removed from the magnet and placed over a tube labeled 'SH2 bound'. Five ml of Miltenyi buffer was added to the column and a syringe plunger was used to push the cells into the tube. Cell counts and viability assays were performed. Cells from the bound and unbound fractions were stained for flow analysis. Unbound and bound cells were placed in culture. Cells were harvested after 14 days. Cells from the light-density cells and the SH2 bound fraction were stained for flow analysis.

TABLE 8

SH2 Cell selection yields

| Fraction | Number of cells | % Yield |
|---|---|---|
| Light-density cells | $2.0 \times 10^8$ | 100 |
| SH2 bound | $3.6 \times 10^6$ | 1.8 |
| SH2 unbound | $2.3 \times 10^8$ | 113 |

TABLE 9

Flow Analysis of the Starting Cell Fractions

| Fraction | % SH2+ cells |
|---|---|
| Light-density cells | 23.9 |
| SH2 bound | 98.3 |
| SH2 unbound | 14.6 |

TABLE 10

Microscopic Examination of P0 Cultures on Day 14

| Fraction | Appearance |
|---|---|
| Light-density cells | 75% confluent, phase bright cells seen |
| SH2 Bound | 90% confluent, phase bright cells seen |
| SH2 Unbound | Very small colonies seen |

TABLE 11

P0 Cell Harvests

| Fraction | Cells seeded/cm$^2$ | Cells harvested/cm$^2$ | % Yield |
|---|---|---|---|
| Light density cells | $8.0 \times 10^4$ | $1.4 \times 10^4$ | 17 |
| SH2 Bound | $8.0 \times 10^4$ | $1.2 \times 10^4$ | 15 |
| SH2 Unbound | $8.0 \times 10^4$ | $3.2 \times 10^2$ | 0.4 |

TABLE 12

Flow analysis of P0 Cultures

| Fraction | % MSC phenotype | % CD45+ cells |
|---|---|---|
| Light-density cells | 99.5 | 0.3 |
| SH2 Bound | 98.7 | 0.2 |

The SH2 cell selection of light-density bone marrow cells using the Miltenyi microbead system yielded less than 2% of the light-density cells in the SH2 bound fraction. The isolation yielded a cell fraction containing cells that were 98.3% SH2+. The SH2 bound cells were 90% confluent with spindle-shaped cells after 14 days in culture under MSC standard culture conditions. The culture of the SH2 bound cells yielded a population of adherent cells that had an MSC phenotype by flow analysis and morphology. Very few adherent cells were isolated from the SH2 unbound cell fraction. These results show that SH2 is an antigen present on the MSC precursor as well as on the culture-expanded MSC.

EXAMPLE 3

MSC Isolation of P0 MSC Cultures using CD45 Cell Selection

P0 MSC cultures have been reported to contain a median of 9% CD45+ cells (range, 0.5 to 50%), while the culture-expanded phenotype of MSCs is CD45 negative. A CD45 selection of P0 cells was performed on three donors to determine if MSCs could be cultured from the CD45 bound cell fraction Anti-CD45 microbeads were from Miltenyi (Lot # NE5848). Large Cell Separation Column was from Miltenyi (Cat # 422-02). Miltenyi buffer: phosphate buffered saline pH 7.2 supplemented with 0.5% BSA and 2 mM EDTA. Flow staining was performed using the manufacturer's suggested instructions. Flow analysis was performed using either the FACS Calibur or the FACS Vantage. Cell viability and cell number were determined using trypan blue.

P0 MSCs were derived from light density human bone marrow cells (donors #394 (0), #386(0) and # 381(0). Samples of $0.5–5.0 \times 10^6$ cells were removed as controls for flow analysis. The remaining cells were diluted to a cell count of $2 \times 10^7$ cells/ml using Milenyi buffer; if the count was $<2 \times 10^7$ cells/ml this step was skipped. Cells were incubated with IgG at 40 ul per ml of cell suspension for 10 minutes at 4° C. with mixing. Cells were centrifuged for 5 minutes at 1100 RPM. The cell pellet was resuspended in Miltenyi buffer (80 ul of buffer per $10^7$ cells). Anti-CD45 microbeads were added (20 ul of beads per $10^7$ cells). The mixture was incubated at 4° C. for 15 minutes with mixing. Miltenyi buffer was added to dilute the mixture and wash the cells. The cells were centrifuged for 10 minutes at 1100 RPM. The cell pellet was resuspended in Miltenyi buffer (0.5 ml of buffer per $10^8$ cells). The Large Cell Separation Column was primed following the manufacturer's instructions. The cell/microbead suspension was added to the column and the suspension drained through the column. The effluent was collected as the 'CD45 unbound' fraction. The column was rinsed three times with 0.5 ml of Miltenyi buffer and this effluent was added to the 'CD45 unbound' fraction. The column was removed from the magnet and placed over a tube labeled 'CD45 bound'. One ml of Miltenyi buffer was added to the column and a syringe plunger used to push the cells into the tube. A fresh large cell column was primed following the manufacturer's instructions and the cells in the 'CD45 bound' tube were added to the second column. The cell/microbead suspension was added to the column and the suspension drained through the column. The effluent was collected as the 'CD45 unbound' fraction. The column was rinsed three times with 0.5 ml of Miltenyi buffer and this effluent was added to the 'CD45 unbound' fraction. The column was removed from the magnet and placed over a tube labeled 'CD45 bound'. One ml of Miltenyi buffer was added to the column and a syringe plunger used to push the cells into the tube. Cell counts and viability assays were performed. Cells from the bound and unbound fractions (# 394) and the unbound fraction (# 386 & # 381) were stained for flow analysis. The cells were placed in culture. Cells were harvested and passaged until an adequate number of cells was available for flow analysis.

TABLE 13

Donor # 381: P0 CD45 Cell selection yields

| Fraction | Number of cells | % Yield |
|---|---|---|
| P0 cells 381 | $8.7 \times 10^6$ | 100 |
| CD45 bound | $1.4 \times 10^5$ | 1.6 |
| CD45 unbound | $4.8 \times 10^6$ | 55 |

TABLE 14

Donor # 386: P0 CD45 Cell selection yields

| Fraction | Number of cells | % Yield |
|---|---|---|
| P0 cells 386 | $1.2 \times 10^7$ | 100 |
| CD45 bound | $2.2 \times 10^5$ | 1.9 |
| CD45 unbound | $8.4 \times 10^6$ | 70 |

TABLE 15

Donor # 394: P0 CD45 Cell selection yields

| Fraction | Number of cells | % Yield |
|---|---|---|
| P0 cells 394 | $1.2 \times 10^8$ | 100 |
| CD45 bound | $1.8 \times 10^6$ | 1.5 |
| CD45 unbound | $1.1 \; 10^8$ | 92 |

TABLE 16

Flow Analysis of the Starting Cell Fractions

| Fraction | % CD45+ cells |
|---|---|
| P0 cells 381 | 4.7 |
| CD45 unbound 381 | 1.5 |
| P0 cells 386 | 1.9 |
| CD45 unbound 386 | 3.5 |
| P0 cells 394 | 2.0 |
| CD45 unbound 394 | 1.4 |

TABLE 17

Donor 381(1) Cell Harvests

| Fraction | Cells/cm² seeded | Cells/cm² harvested | Days in culture | Fold Expansion |
|---|---|---|---|---|
| CD45 bound | $3.4 \times 10^4$ | $5.8 \times 10^4$ | 12 | 1.7 |
| CD45 unbound | $5.4 \times 10^4$ | $8.3 \times 10^3$ | 7 | 1.5 |

TABLE 18

Donor 381(2) CD45 bound Cell Harvest

| Fraction | Cells/cm² seeded | Cells/cm² harvested | Days in culture | Fold Expansion |
|---|---|---|---|---|
| CD45 bound | $2.9 \times 10^3$ | $3.7 \times 10^4$ | 3 | 12.8 |

TABLE 19

Donor 386(1) Cell Harvests

| Fraction | Cells/cm² seeded | Cells/cm² harvested | Days in culture | Fold Expansion |
|---|---|---|---|---|
| CD45 bound | $4.4 \times 10^4$ | $7.5 \times 10^4$ | 12 | 1.7 |
| CD45 unbound | $5.4 \times 10^3$ | $1.6 \times 10^4$ | 7 | 3.0 |

TABLE 20

Donor 394(1) Cell Harvests

| Fraction | Cells/cm² seeded | Cells/cm² harvested | Days in culture | Fold Expansion |
|---|---|---|---|---|
| CD45 bound | $5.3 \times 10^3$ | $1.3 \times 10^4$ | 11 | 2.5 |
| CD45 unbound | $5.3 \times 10^3$ | $3.1 \times 10^4$ | 11 | 5.0 |

TABLE 21

Flow Analysis of Cells Cultured from CD45 Selected P0 MSCs

| Fraction | % MSC phenotype | % CD45+ |
|---|---|---|
| 381(2) from CD45 bound | 99.2 | 0.7 |
| 386(1) from CD45 bound | 99.0 | 0.8 |
| 394(1) from CD45 bound | 98.5 | 1.4 |

The CD45 selection of P0 MSCs yielded a cell population which was <2% of the starting P0 population. Cultured CD45 bound cells isolated from the P0 MSCs yielded MSCs as defined by flow cytometry and morphology. The CD45 unbound cell fraction isolated from the P0 MSCs also yielded MSCs as defined by flow cytometry and morphology. The phenotype of the MSC precursor appeared to be CD45 dim.

EXAMPLE 4
MSC Isolation using CD45 Selection

Light-density cells isolated from bone marrow were selected using directly conjugated anti-CD45 Miltenyi microbeads (Miltenyi Lot # NE5848) following the manufacturer's instructions. VS Column was from Miltenyi (Lot # 0231). Pre-separation filters 30 um were from Miltenyi (Lot 55). Miltenyi buffer: phosphate buffered saline pH 7.2 supplemented with 0.5% BSA and 2 mM EDTA. Flow staining was performed using the manufacturer's suggested instructions. Flow analysis was performed using either the FACS Calibur or the FACS Vantage. Cell viability and cell number were determined using trypan blue.

Light density cells were isolated from human bone marrow aspirate (donor # 358) using Dendreon solution BDS72 following density centrifugation of the bone marrow aspirates. Aliquots were removed as controls for flow analysis and cell culture. The remaining cells were diluted to a cell count of $2 \times 10^7$ cells/ml using Miltenyi buffer. Cells were incubated with IgG at 40 ul per ml of cell suspension for 10 minutes at 4° C. with mixing. Cells were centrifuged for 10 minutes at 1000 RPM. The cell pellet was resuspended in Miltenyi buffer (80 ul of buffer per $10^7$ cells). Anti-CD45 microbeads were added (20 ul of beads per $10^7$ cells). The mixture was incubated at 4° C. for 20 minutes with mixing. Miltenyi buffer was added to dilute the mixture and wash the cells. The cells were centrifuged for 10 minutes at 1000 RPM. The cell pellet was resuspended in Miltenyi buffer (0.5 ml of buffer per $10^8$ cells). The VS column was primed following the manufacturer's instructions. The pre-filter was primed following the manufacturer's instructions. The cell/microbead suspension was added to the pre-filter and the suspension drained through the column. The effluent was collected as the 'CD45 unbound' fraction. The column was rinsed twice with 3 ml of Miltenyi buffer and this effluent was added to the 'CD45 unbound' fraction. The column was removed from the magnet and placed over a tube labeled 'CD45 bound'. Five ml of Miltenyi buffer was added to the column and a syringe plunger was used to push the cells into the tube. A fresh column was primed and the cells in the 'CD45 bound' tube were added to the second column. The pre-filter was primed following the manufacturer's instructions. The cell/microbead suspension was added to the pre-filter and the suspension drained through the column. The effluent was collected as the 'CD45 unbound' fraction. The column was rinsed twice with 3 ml of Miltenyi buffer and this effluent was added to the 'CD45 unbound' fraction. The column was removed from the magnet and placed over a tube labeled 'CD45 bound'. Five ml of Miltenyi buffer was added to the column and a syringe plunger was used to push the cells into the tube. Cell counts and viability assays were performed. Cells from the bound and unbound fractions were stained for flow analysis. Cells were placed in culture. Cells were harvested and counted.

TABLE 22

CD45 Cell selection yields

| Fraction | Number of cells | % Yield |
|---|---|---|
| Light-density cells | $3.93 \times 10^8$ | 100 |
| CD45 bound | $1.84 \times 10^8$ | 47 |
| CD45 unbound | $1.37 \times 10^8$ | 35 |

TABLE 23

Flow analysis of the Starting Cell Fractions

| Fraction | % CD45+ cells |
|---|---|
| Light-density cells | 78.3 |
| CD45 bound | 99.0* |
| CD45 unbound | 51.5 |

* the staining intensity is significantly enhanced in the CD45 bound cell fraction

TABLE 24

Microscopic Examination of P0 Cultures on Day 14

| Fraction | Appearance |
|---|---|
| Light-density cells | 100% confluent, many phase bright cells |
| CD45 bound | 80% confluent, some phase bright cells |
| CD45 unbound | 95% confluent, some phase bright cells |

TABLE 25

P0 Cell Harvests

| Fraction | Cells/cm² seeded | Cells/cm² harvested | % Yield |
|---|---|---|---|
| Light-density cells | $1.6 \times 10^5$ | $5.4 \times 10^4$ | 33 |
| CD45 bound | $1.6 \times 10^5$ | $1.9 \times 10^4$ | 12 |
| CD45 unbound | $1.6 \times 10^5$ | $4.6 \times 10^4$ | 29 |

Forty-seven percent of the cells were present in the CD45 bound fraction. This CD45 bound cell population was 99% CD45 positive by flow analysis and was capable of yielding MSCs at P0 as defined by morphology. The CD45 unbound cell fraction was 35% of the total cells selected and was 51.5% CD45 positive. The fluorescence intensity of the CD45 unbound cells was much lower than that of the CD45 bound cells. This cell fraction was also capable of yielding MSCs in P0 culture as defined by morphology. This experiment provides further evidence that the MSC precursor is CD45 positive with a dim staining intensity.

EXAMPLE 5
MSC Isolation using Fibroblast Cell Selection

Anti-fibroblast microbeads were developed for the separation of cells based on the expression of a fibroblast-specific antigen. Since cultured MSCs have a fibroblastic morphology, the anti-fibroblast microbeads were used to select a fraction of cells from light-density bone marrow cells. Cells that were bound and those that were not bound were placed in standard MSC culture conditions and observed.

Anti-fibroblast microbeads were from Miltenyi (Lot # NE630). VS Column was from Miltenyi (Lot # 0231). Pre-separation filters 30 um were from Miltenyi (Lot # 55). Miltenyi buffer: phosphate buffered saline pH 7.2 supplemented with 0.5% BSA and 2 mM EDTA. Flow staining was performed following the manufacturer's suggested instructions. Flow analysis was performed using either the FACS Calibur or the FACS Vantage. Cell viability and cell number were determined using trypan blue.

Assays were performed as follows to measure the osteogenic and adipogenic potential of the cells.

Adipogenesis assay. Cells were plated in a 6-well dish ($2\times10^5$ cells/well) in hMSC media. Confluent MSCs were pulse induced with high glucose media containing dexamethasone, insulin, 3-isobutyl-1-methyl-xanthine and indomethacin. At the end of the culture period the plates were fixed with 10% formalin, stained with Oil Red "O" and counterstained with hematoxylin. The formation of lipid vacuoles which stain red were observed and semi-quantitated by percent of well surface area.

Osteogenic calcium deposition assay. Cells were plated in 6-well dishes ($3\times10^4$ cells/well). Wells labeled as "OS" were fed with hMSC media containing supplements of Ascorbic acid-2-phosphate, dexamethasone and β-glycerophosphate. Wells labeled as "Control" were fed with standard hMSC media. Media changes were performed twice weekly for 14 to 16 days The increased calcium deposition was measured through semi-quantitative colorimetric assays.

Light density cells were isolated from human bone marrow aspirates (donors #373, # 386 & # 421) using Dendreon solution BDS72 following density centrifugation of the bone marrow aspirates. Aliquots were removed as controls for cell culture. The remaining cells were diluted to a cell count of $2\times10^7$ cells/ml using Miltenyi buffer. Cells were incubated with IgG at 40 ul per ml of cell suspension for 10 minutes at 4° C. with mixing. Cells were centrifuged for 10 minutes at 1000 RPM. The cell pellet was resuspended in Miltenyi buffer (80 ul of buffer per $10^7$ cells). Anti-fibroblast microbeads were added (20 ul of beads per $10^7$ cells). The mixture was incubated at room temperature for 30 minutes with mixing. Miltenyi buffer was added to dilute the mixture and wash the cells. The cells were centrifuged for 10 minutes at 1000 RPM. The cell pellet was resuspended in Miltenyi buffer (1 ml of buffer per $10^8$ cells). The VS column was primed following the manufacturer's instructions. The pre-filter was primed following the manufacturer's instructions. The cell/microbead suspension was added to the pre-filter and the suspension drained through the column. The effluent was collected as the 'fibroblast unbound' fraction. The column was rinsed twice with 3 ml of Miltenyi buffer and this effluent was added to the 'fibroblast unbound' fraction. The column was removed from the magnet and placed over a tube labeled 'fibroblast bound'. Five ml of Miltenyi buffer was added to the column and a syringe plunger was used to push the cells into the tube. A fresh column was primed and the cells in the 'fibroblast bound' tube were added to the second column. The pre-filter was primed following the manufacturer's instructions. The cell/microbead suspension was added to the pre-filter and the suspension drained through the column. The effluent was collected as the 'fibroblast unbound' fraction. The column was rinsed twice with 3 ml of Miltenyi buffer and this effluent was added to the 'fibroblast unbound' fraction. The column was removed from the magnet and placed over a tube labeled 'fibroblast bound'. Five ml of Miltenyi buffer was added to the column and a syringe plunger was used to push the cells into the tube. Cell counts and viability assays were performed. Cells from donors 373 and 386 were placed in culture. Cells were harvested and passaged. P0 cells from the light density control and the fibroblast bound cultures from donor 373 were stained for flow analysis. P0 cells from donor 386 were placed into the in vitro osteogenic differentiation assay and the in vitro adipogenic assay. Cultures from the adipogenic assays showed significant adipogenesis of the MSCs.

TABLE 26

Donor 373 Cell selection yields

| Fraction | Number of cells | % Yield |
|---|---|---|
| Light-density cells | $6.0 \times 10^7$ | 100 |
| Fibroblast bound | $5.6 \times 10^6$ | 9 |
| Fibroblast unbound | $4.2 \times 10^7$ | 70 |

TABLE 27

Donor 386 Cell selection yields

| Fraction | Number of cells | % Yield |
|---|---|---|
| Light-density cells | $6.0 \times 10^8$ | 100 |
| Fibroblast bound | $2.1 \times 10^7$ | 3.5 |
| Fibroblast unbound | $4.3 \times 10^8$ | 72 |

TABLE 28

Donor 421 Cell selection yields

| Fraction | Number of cells | % Yield |
|---|---|---|
| Light-density cells | $4.4 \times 10^8$ | 100 |
| Fibroblast bound | $2.6 \times 10^7$ | 5.8 |
| Fibroblast unbound | $4.2 \times 10^8$ | 94 |

TABLE 29

Donor 373 Microscopic Examination of P0 Cultures on Day 14

| Fraction | Appearance |
|---|---|
| Light-density cells | 80% confluent, phase bright cells seen |
| Fibroblast bound | 50% confluent, phase bright cells seen |
| Fibroblast unbound | Round cells, debris |

TABLE 30

Donor 386 Microscopic Examination of P0 Cultures on Day 14

| Fraction | Appearance |
|---|---|
| Light-density cells | 100% confluent, phase bright cells seen |
| Fibroblast bound | 100% confluent, phase bright cells seen |
| Fibroblast unbound | Round floating cells, debris |

TABLE 31

Donor 373 P0 Cell Harvests

| Fraction | Cells seeded/cm$^2$ | Cells harvested/cm$^2$ | % Yield |
|---|---|---|---|
| Light-density cells | $8.1 \times 10^4$ | $1.2 \times 10^4$ | 15 |
| Fibroblast bound | $8.0 \times 10^4$ | $5.0 \times 10^3$ | 10 |
| Fibroblast unbound | $8.1 \times 10^4$ | $3.2 \times 10^1$ | 0.04 |

TABLE 32

Donor 386 PO Cell Harvests

| Fraction | Cells seeded/cm$^2$ | Cells harvested/cm$^2$ | % Yield |
| --- | --- | --- | --- |
| Light-density cells | $1.6 \times 10^5$ | $1.6 \times 10^4$ | 10 |
| Fibroblast bound | $1.6 \times 10^5$ | $1.8 \times 10^4$ | 11 |
| Fibroblast unbound | $1.6 \times 10^5$ | $3.2 \times 10^1$ | 0.02 |

TABLE 33

Donor 373 Flow analysis of PO Cultures

| Donor/Fraction | % MSC phenotype | % CD45+ cells |
| --- | --- | --- |
| 373(0) light-density cells | 89.3 | 10.3 |
| 373(0) fibroblast bound cells | 85.9 | 13.8 |

Figure 2:
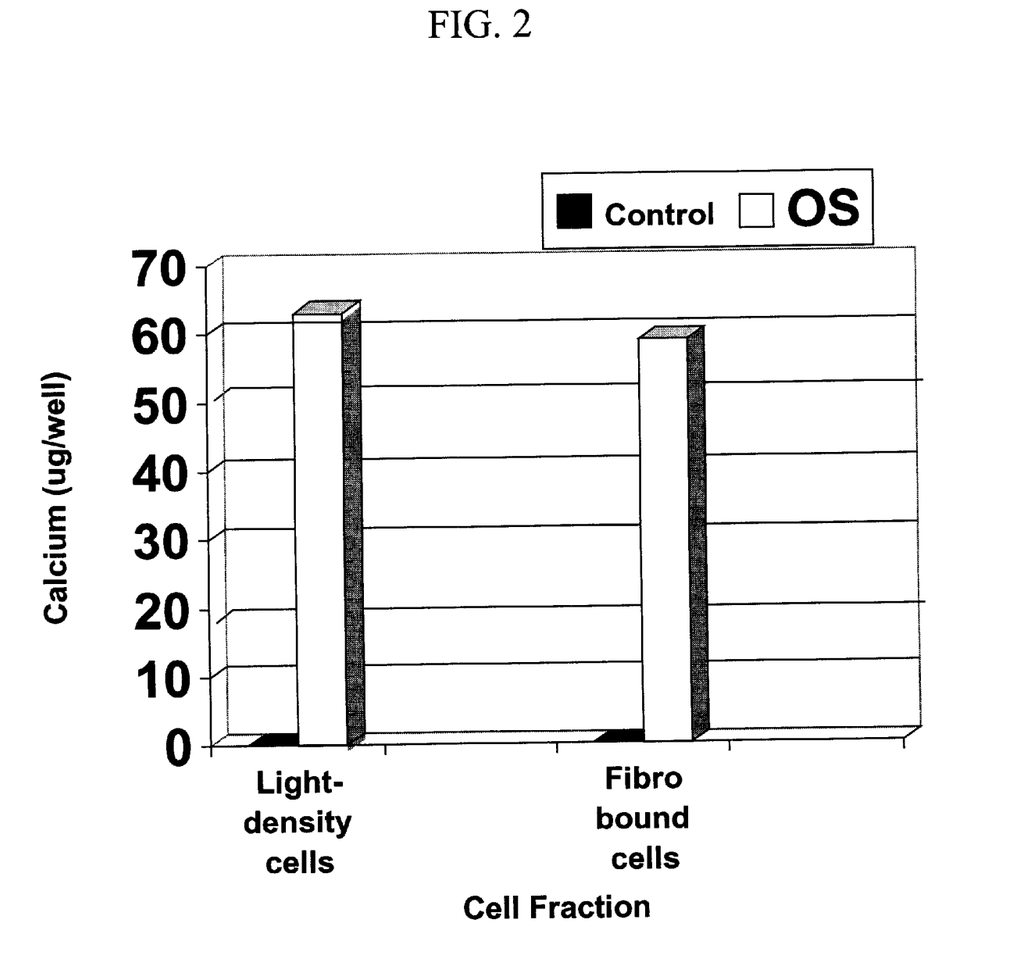
FIG. 2 shows the results of the calcium deposition assay described in Example 5.

The results of the calcium assay for Donor 386(1), Light-density cell and fibroblast bound cell fractions are shown in Table 34 and FIG. 2.

TABLE 34

| | | | Spectrophotometer OD Readings at 575 nm | | | Calcium ($\mu$g/well) | | | | |
| --- | --- | --- | --- | --- | --- | --- | --- | --- | --- | --- |
| Sample ID | Condition | Dilution Factor | 1 | 2 | 3 | 1 | 2 | 3 | Mean | S.D. |
| Light density | Control | 20 | 0.0000 | 0.0000 | 0.0000 | 0.0 | 0.0 | 0.0 | 0.0 | 0.0 |
| Light density | OS | 50 | 0.1490 | 0.1625 | 0.1903 | 60.4 | 62.3 | 66.4 | 63.0 | 3.1 |
| Fibro Pos | Control | 20 | 0.0000 | 0.0000 | 0.0000 | 0.0 | 0.0 | 0.0 | 0.0 | 0.0 |
| Fibro Pos | OS | 50 | 0.1370 | 0.1554 | 0.1225 | 58.6 | 61.3 | 56.5 | 58.8 | 2.4 |

The fibroblast bound cell fraction of light density bone marrow cells represented 3–9% of the starting nucleated cell population and adhered to polystyrene. Under standard MSC culture conditions, the fibroblast bound cell fraction yielded an MSC population as defined by flow cytometry, biological assays and morphology.

EXAMPLE 6
MSC Isolation using Fibroblast and CD14 Cell Selection

Anti-fibroblast microbeads were from Miltenyi (Lot # NE6836). VS Column was from Miltenyi (Lot # 0231). Pre-separation filters 30 um were from Miltenyi (Lot # 55). Miltenyi buffer: phosphate buffered saline pH 7.2 supplemented with 0.5% BSA and 2 mM EDTA. Anti-CD14 magnetic beads were from Dynal (Lot # A93900). Flow staining was performed following the manufacturer's suggested instructions. Flow analysis was performed using either the FACS Calibur or the FACS Vantage. Cell viability and cell number were determined using trypan blue.

Light density cells were isolated from a human bone marrow aspirate (donor #391) using Dendreon solution BDS72 following density centrifugation of the bone marrow aspirates. Aliquots were removed as controls for cell culture. The remaining cells were diluted to a cell count of $2 \times 10^7$ cells/ml using Miltenyi buffer. Cells were incubated with IgG at 40 ul per ml of cell suspension for 10 minutes at 4° C. with mixing. Cells were centrifuged for 10 minutes at 1000 RPM. The cell pellet was resuspended in Miltenyi buffer (80 ul of buffer per $10^7$ cells). Anti-fibroblast microbeads were added (20 ul of beads per $10^7$ cells). The mixture was incubated at 4° C. for 15 minutes with mixing. Miltenyi buffer was added to dilute the mixture and wash the cells. The cells were centrifuged for 10 minutes at 1000 RPM. The cell pellet was resuspended in Miltenyi buffer (1 ml of buffer per $10^8$ cells). The VS column was primed following the manufacturer's instructions. The pre-filter was primed following the manufacturer's instructions. The cell/microbead suspension was added to the pre-filter and the suspension drained through the column. The effluent was collected as the 'fibroblast unbound' fraction. The column was rinsed twice with 3 ml of Miltenyi buffer and this effluent was added to the 'fibroblast unbound' fraction. The column was removed from the magnet and placed over a tube labeled 'fibroblast bound'. Five ml of Miltenyi buffer was added to the column and a syringe plunger used to push the cells into the tube. A fresh column was primed and the cells in the 'fibroblast bound' tube were added to the second column. The pre-filter was primed following the manufacturer's instructions. The cell/microbead suspension was added to the pre-filter and the suspension drained through the column. The effluent was collected as the 'fibroblast unbound' fraction. The column was rinsed twice with 3 ml of Miltenyi buffer and this effluent was added to the 'fibroblast unbound' fraction. The column was removed from the magnet and placed over a tube labeled 'fibroblast bound'. Five ml of Miltenyi buffer was added to the column and a syringe plunger used to push the cells into the tube. Cell counts and viability assays were performed. Unbound cells were placed in culture. Bound cells were incubated with Dynal Anti-CD14 magnetic beads at a cell concentration of $2 \times 10^7$ cells per ml and a bead concentration of $2 \times 10^7$ beads per ml for 1 hour at 4° C. with mixing. The cell bead suspension was placed next to the Dynal hand magnet for 2 minutes. After 2 minutes, the unattached cells were decanted into a tube labeled 'CD14 unbound'. The cell/bead tube was removed from the magnet and 5 ml of buffer added to resuspend the cells. The cell/bead suspension was placed next to the Dynal hand magnet for 2 minutes. After 2 minutes, the unattached cells were decanted into a tube labeled 'CD14 unbound'. The cell/bead tube was removed from the magnet and 5 ml of buffer added to resuspend the cells. The cell/bead suspension was placed next to the Dynal hand magnet for 2 minutes. After 2 minutes, the unattached cells were decanted into a tube labeled 'CD14 unbound'. The cell/bead tube was removed from the magnet and 5 ml of buffer added to resuspend the cells. The cells that remained attached to beads were counted and placed into culture in two 10 cm$^2$ wells. The cells in the unbound tube were placed next to the hand magnet for 2 minutes. Unattached cells were decanted, counted and plated into one 10 cm$^2$ well. Cells were harvested after 14 days. Cells cultured from the light-density cells and the Fibroblast bound/CD14 bound fractions were stained for flow analysis.

TABLE 35

Fibroblast Cell selection yields

| Fraction | Number of cells | % Yield |
|---|---|---|
| Light-density cells | $3.35 \times 10^8$ | 100 |
| Fibroblast bound | $1.2 \times 10^7$ | 3.4 |
| Fibroblast unbound | $3.51 \times 10^8$ | 105 |

TABLE 36

CD14 Cell selection yields

| Fraction | Number of cells | % Yield |
|---|---|---|
| Fibroblast bound | $9 \times 10^6$ | 100 |
| CD14 bound | $3.4 \times 10^6$ | 38 |
| CD14 unbound | $1.9 \times 10^6$ | 21 |

TABLE 37

Microscopic Examination of P0 Cultures on Day 14

| Fraction | Appearance |
|---|---|
| Light-density cells | 100% confluent, phase bright cells seen |
| Fibroblast unbound | Round cells as singles and clumps |
| Fibroblast bound/CD14 bound | 100% confluent with beads attached to some spindle shaped cells |
| Fibroblast bound/CD14 unbound | Round cells in singles and clumps |

TABLE 38

P0 Cell Harvests

| Fraction | Cells seeded/cm² | Cells harvested/cm² | % Yield |
|---|---|---|---|
| Light-density cells | $1.6 \times 10^5$ | $7.6 \times 10^4$ | 47 |
| Fibroblast unbound | $1.6 \times 10^5$ | $1.6 \times 10^2$ | 0.1 |
| Fibroblast bound/CD14 bound | $1.7 \times 10^5$ | $4.0 \times 10^4$ | 23 |
| Fibroblast bound/CD14 unbound | $1.9 \times 10^5$ | $1.0 \times 10^3$ | 0.5 |

TABLE 39

Flow analysis of P0 Cultures

| Fraction | % MSC phenotype | % CD45 + cells |
|---|---|---|
| Light-density cells | 98.1 | 1.0 |
| Fibroblast bound/CD14 bound | 98.3 | 0.3 |

In order to further define the phenotype of the MSC precursor, a sequential cell selection was performed using Miltenyi microbeads to select fibroblast bound cells, followed by the use of Dynal magnetic beads to isolate CD14 bound cells from the fibroblast bound fraction. This is possible since the size of the microbead is too small to interfere with the Dynal selection.

Using this technique, the fibroblast bound/CD14 bound cell fraction was approximately 1.3% of the starting light-density cell population. The fibroblast bound/CD14 bound cells, when placed in standard MSC culture conditions, adhered to polystyrene flasks and after 14 days of culture, yielded a MSC population as defined by flow analysis and morphology.

Based on this single selection, it would appear that the MSC precursor is a fibroblast+, CD14+ cell. This is unexpected since the culture expanded MSC is a fibroblast+, CD14 negative cell.

EXAMPLE 7

MSC Isolation using Fibroblast Cell Selection and Flow Sorting

Anti-fibroblast microbeads were from Miltenyi (Lot # NE7105). VS Column was from Miltenyi (Lot # 0231). Pre-separation filters 30 um were from Miltenyi (Lot # 55). Miltenyi buffer: phosphate buffered saline pH 7.2 supplemented with 0.5% BSA and 2 mM EDTA. Flow staining was performed following the manufacturer's suggested instructions. Flow analysis was performed using either the FACS Calibur or the FACS Vantage. Flow sorting was performed on the FACS Vantage. Determination of cell viability and cell number was done using trypan blue). Osteogenic potential was measured using the method described in Example 5 and with an in vivo osteogenic cube assay as described for example in U.S. Pat. No. 5,486,359. Adipogenic assays were performed according to methods described in Example 5.

The chondrogenesis assays was performed as follows. Cells were pelleted in a 15 ml conical tube ($2.5 \times 10^5$ cells/pellet) in chondrogenic media, consisting of high glucose, dexamethasone and TGF-β3. The pellets were submitted to histology for embedding, thin sectioning and histochemical staining. The presence Qf chondrocytes was detected using Toluidine Blue, which stains for proteoglycans and with an antibody specific for type II collagen.

Light density cells were isolated from human bone marrow aspirate (donors # 401 and # 438) using Dendreon solution BDS72 following density centrifugation of the bone marrow aspirates. Aliquots were removed as controls for flow analysis and cell culture. The remaining cells were diluted to a cell count of $2 \times 10^7$ cells/ml using Miltenyi buffer. Cells were incubated with IgG at 40 ul per ml of cell suspension for 10 minutes at 4° C. with mixing. Cells were centrifuged for 10 minutes at 1000 RPM. The cell pellet was resuspended in Miltenyi buffer (80 ul of buffer per $10^7$ cells). Anti-fibroblast microbeads were added (20 ul of beads per $10^7$ cells). The mixture was incubated at room temperature for 30 minutes with mixing. Miltenyi buffer was added to dilute the mixture and wash the cells. The cells were centrifuged for 10 minutes at 1000 RPM. The cell pellet was resuspended in Miltenyi buffer (1 ml of buffer per $10^8$ cells). The VS column was primed following the manufacturer's instructions. The pre-filter was primed following the manufacturer's instructions. The cell/microbead suspension was added to the pre-filter and the suspension drained through the column. The effluent was collected as the 'fibroblast unbound' fraction. The column was rinsed twice with 3 ml of Miltenyi buffer and this effluent was added to the 'fibroblast unbound' fraction. The column was removed from the magnet and placed over a tube labeled 'fibroblast bound'. Five ml of Miltenyi buffer was added to the column and a syringe plunger was used to push the cells into the tube. A fresh column was primed and the cells in the 'fibroblast bound' tube was added to the second column. The pre-filter was primed following the manufacturer's instructions. The cell/microbead suspension was added to the pre-filter and the suspension drained through the column. The effluent was collected as the 'fibroblast unbound' fraction. The column was rinsed twice with 3 ml of Miltenyi buffer and this effluent was added to the 'fibroblast unbound' fraction. The column was removed from the magnet and placed over a tube labeled 'fibroblast bound'. Five ml of Miltenyi buffer was added to the column and a syringe plunger was used to push the cells into the tube. Cell counts and viability assays were performed.

Cells from the fibroblast unbound fraction were stained for flow analysis. Cells from the fibroblast bound fraction were incubated with anti-SH3, anti-CD45 and anti-CD14. Cells were sorted: Donor 401 was sorted into two groups: population 1 and population 2. Donor 438 was sorted into three groups: population 1, population 1a and population 2. Cells from the fibroblast unbound fraction (Donor 401 only) and the sorted populations were placed in culture. P0 cells were harvested and passaged. P1 cells from the light-density and population 1 cultures on donor # 401 were stained for flow cytometry and placed in the in vivo cube assay. P1 cells for donor # 438 were passaged. P2 cells from the light density, population 1 and population 1a cultures on donor # 438 were stained for flow cytometry and placed in the in vitro biological assays (osteogenic, adipogenic and chondrogenic).

TABLE 40

Donor 401 Cell selection yields

| Fraction | Number of cells | % Yield |
|---|---|---|
| Light-density cells | $6.6 \times 10^8$ | 100 |
| Fibroblast bound | $2.9 \times 10^7$ | 4.4 |
| Fibroblast unbound | $5.4 \times 10^8$ | 82 |

TABLE 41

Donor 438 Cell selection yields

| Fraction | Number of cells | % Yield |
|---|---|---|
| Light-density cells | $8.5 \times 10^8$ | 100 |
| Fibroblast bound | $2.0 \times 10^7$ | 2.4 |
| Fibroblast unbound | $7.9 \times 10^8$ | 93 |

TABLE 42

Fibroblast Bound Cells after Flow Sorting

| Fraction | Surface Phenotype Flow Profile | Number of Cells |
|---|---|---|
| Donor 401 Population 1 | SH3 + bright; CD14 dim | $1.1 \times 10^4$ |
| Donor 401 Population 2 | SH3 + bright; CD14 bright | $2.0 \times 10^4$ |
| Donor 438 Population 1 | SH3 + bright; CD14 dim | $1.5 \times 10^4$ |
| Donor 438 Population 1a | SH3 + bright; CD45 dim | $1.5 \times 10^4$ |
| Donor 438 Population 2 | SH3 + bright; CD14 bright | $4.8 \times 10^5$ |

TABLE 43

Donor 401: Microscopic Examination of P0 Cultures on Day 12

| Fraction | Appearance |
|---|---|
| Light-density cells | 60% confluent, phase bright cells seen |
| Fibroblast unbound | Round cells with rare spindle shaped cells seen |
| Fibroblast bound Population 1 | 100% confluent, phase bright cell seen |
| Fibroblast bound Population 2 | Round cells with rare spindle shaped cells seen |

TABLE 44

Donor 438: Microscopic Examination of P0 Cultures on Day 14

| Fraction | Appearance |
|---|---|
| Light-density cells | 90% confluent, phase bright cells seen |
| Fibroblast bound Population 1 | 100% confluent, phase bright cells seen |
| Fibroblast bound Population 1a | 100% confluent, phase bright cells seen |
| Fibroblast bound Population 2 | Debris |

TABLE 45

Donor 401: P0 (Day 12 cultures) Cell Harvests

| Fraction | Cells Seeded/cm² | Cells Harvested/cm² | % Yield |
|---|---|---|---|
| Light-density cells | $8.0 \times 10^4$ | $1.7 \times 10^4$ | 21 |
| Fibroblast unbound | $8.0 \times 10^4$ | $6.7 \times 10^2$ | 0.08 |
| Population 1 | $8.9 \times 10^2$ | $1.7 \times 10^3$ | 196 |
| Population 2 | $1.7 \times 10^3$ | $7.1 \times 10^2$ | 42 |

TABLE 46

Donor 438: P0 (Day 14 cultures) Cell Harvests

| Fraction | Cells Seeded/cm² | Cells Harvested/cm² | Fold Expansion |
|---|---|---|---|
| Light-density cells | $8.0 \times 10^4$ | $4.5 \times 10^4$ | 0.6 |
| Population 1 | $6.0 \times 10^2$ | $4.2 \times 10^4$ | 70 |
| Population 1a | $6.0 \times 10^2$ | $4.6 \times 10^4$ | 77 |
| Population 2 | $9.6 \times 10^3$ | 0 | 0 |

TABLE 47

P1 (Day 7 cultures) Cell Harvests

| Fraction | Cells Seeded/cm² | Cells Harvested/cm² | Fold Expansion |
|---|---|---|---|
| 401 Light-density cells | $6.7 \times 10^3$ | $3.6 \times 10^4$ | 5 |
| 401 Population 1 | $0.3 \times 10^3$ | $2.5 \times 10^4$ | 90.0 |
| 438 Light-density cells | $6.1 \times 10^3$ | $2.3 \times 10^4$ | 4 |
| 438 Population 1 | $5.7 \times 10^3$ | $2.1 \times 10^4$ | 4 |
| 438 Population 1a | $6.2 \times 10^3$ | $2.6 \times 10^4$ | 5 |

TABLE 48

Flow analysis of P1 Cultures Donor 401(1)

| Fraction | % MSC phenotype | % CD45+ |
|---|---|---|
| Light-density cells | 99.2 | 0.2 |
| Population 1 | 99.8 | <0.1 |

TABLE 49

In vivo Cube Assay Results Donor 401(1)

| Fraction | Average Score for 3 cubes |
|---|---|
| Light-density cells | 0.3 |
| Population 1 | 0.5 |
| Negative Control | 0 |

TABLE 50

Donor 438: P2 (Day 7 cultures) Cell Harvest

| Fraction | Cells seeded/cm$^2$ | Cells Harvests/cm$^2$ | Fold Expansion |
|---|---|---|---|
| Light-density cells | 5.4 × 10$^3$ | 2.1 × 10$^4$ | 3.8 |
| Population 1 | 5.3 × 10$^3$ | 2.4 × 10$^4$ | 4.5 |
| Population 1a | 5.3 × 10$^3$ | 2.2 × 10$^4$ | 4.2 |

TABLE 51

Flow analysis of P2 Cultures Donor 438(2)

| Fraction | % MSC phenotype | % CD45+ |
|---|---|---|
| Light-density cells | 99.9 | <0.1 |
| Population 1 | 99.9 | <0.1 |
| Population 1a | 99.9 | <0.1 |

TABLE 52

Donor 438(2): Adipogenesis Results

| | % Area with Vacuoles | | |
|---|---|---|---|
| Fraction | Adipogenic Medium | Adipogenic Maintenance Medium | Human MSC Medium |
| Light-density cells | 40 | 0 | 0 |
| Population 1 | 40 | 0 | 0 |
| Population 1a | 40 | 0 | 0 |

All samples measured positive as evaluated by established acceptance criteria.

TABLE 53

Donor 438(2): Osteogenesis Results

| | Calcium ug/dish | | Calcium ug/million cells | |
|---|---|---|---|---|
| Fraction | Control | OS | Control | OS |
| Light-density cells | 1.0 | 16.2 | 5.1 | 12.9 |
| Population 1 | 1.1 | 18.0 | 7.2 | 15.1 |
| Population 1a | 1.1 | 14.4 | 5.8 | 12.8 |

All samples measured positive as evaluated by established acceptance criteria.

TABLE 54a

Donor 438(2): Chondrogenesis Results; Toluidine Blue Results

| | Toluidine Blue (%) | | | |
|---|---|---|---|---|
| Fraction | Day 7 | Day 14 | Day 21 | Day 28 |
| Light-density cells | 60 | 40 | 70 | 100 |
| Population 1 | 70 | 100 | 90 | 100 |
| Population 1a | 90 | 100 | 100 | 100 |

TABLE 54b

Donor 438(2): Chondrogenesis Results; Collagen Type II Results

| | Anti-Collagen Type II (%) | | | |
|---|---|---|---|---|
| Fraction | Day 7 | Day 14 | Day 21 | Day 28 |
| Light-density cells | 0 | 0 | 30 | 50 |
| Population 1 | 0 | 100 | 70 | 80 |
| Population 1a | 0 | 90 | 100 | 80 |

TABLE 54c

Donor 438(2): Chondrogenesis Results; Pellet Size

| | Diameter (millimeters) | | | |
|---|---|---|---|---|
| Fraction | Day 7 | Day 14 | Day 21 | Day 28 |
| Light-density cells | 1.0 | 0.8 | 0.9 | 1.0 |
| Population 1 | 0.8 | 1.2 | 1.5 | 1.5 |
| Population 1a | 1.0 | 1.4 | 1.6 | 1.5 |

All samples measured positive as evaluated by established acceptance criteria.

To further define the phenotype of the MSC precursor, fibroblast bound light-density bone marrow cells were stained with anti-SH3 and anti-CD14 and sorted using flow cytometry.

This resulted in the sorting of population 1, population 1a and population 2. All three of these populations were SH3+ bright. Population 1 was CD14+ with a dim staining intensity. Population 1a was CD45+ with a dim staining intensity. Population 2 was CD14+ with a bright staining intensity. MSCs were cultured from Population 1 and Population 1a cell fractions, as confirmed from flow analysis and in vitro and in vivo biological assays. It was estimated that one Population 1/1a cell is present in 10$^5$ light-density bone marrow cells.

What is claimed is:

1. An isolated population of human mesenchymal stem cells comprising human mesenchymal stem cells which have been enriched for CD45+ human mesenchymal stem cells.

2. The isolated population of human mesenchymal stem cells of claim 1 wherein the human mesenchymal stem cells which are CD45+ are further reactive with at least one monoclonal antibody selected from the group consisting of SH2 antibody, SH3 antibody and SH4 antibody.

3. The isolated cell population of claim 2 wherein the human mesenchymal stem cells are SH3+ and CD45+.

4. The isolated cell population of claim 2 wherein the human mesenchymal stem cells are SH2+ and CD45+.

5. A composition comprising an isolated population of human mesenchymal stem cells which bear a fibroblast surface marker and have been enriched for CD45+ human mesenchymal stem cell.

6. The composition of claim 5 further comprising CD14+ cells.

7. A process of isolating a population of human mesenchymal stem cells which are CD45+, comprising
   (a) obtaining an enriched population of human mesenchymal stem cells; and
   (b) selecting from the cell population of (a) cells that are CD45+.

8. A process of isolating a population of human mesenchymal stem cells which are SH3+ and CD45+, comprising
   (a) obtaining an enriched population of human mesenchymal stem cells that are SH3+; and (b) selecting from the cell population of (a) cells that are CD45+.

9. A process of isolating a population of human mesenchymal stem cells which are SH2+ and CD45+, comprising
   (a) obtaining an enriched population of human mesenchymal stem cells that are SH2+; and
   (b) selecting from the cell population of (a) cells that are CD45+.

10. A process of isolating a population of human mesenchymal stem cells which bear fibroblast surface markers comprising
    (a) obtaining an enriched population of human mesenchymal stem cells; and
    (b) selecting from the cell population of (a) cells that are fibroblast+.

11. The method of claim 10, further comprising selecting from the cell population bearing fibroblast surface markers cells that are SH3+.

12. The method of claim 11, further comprising selecting from the cell population bear fibroblast surface markers and are SH3+, cells that are CD45+.

13. A method for treating a patient in need of mesenchymal stem cells, comprising administering human mesenchymal stem cells which are CD45+ to said patient.

14. The method of claim 13 wherein the human mesenchymal stem cells are SH3+ and CD45+.

15. The method of claim 13 wherein the human mesenchymal stem cells are SH2+ and CD45+.

16. The method of claim 13 wherein the mesenchymal stem cells are administered to generate bone formation.

17. The method of claim 13 wherein the mesenchymal stem cells are administered to treat or repair a connective tissue defect in the patient.

18. The method of claim 17 wherein the defect is a bone defect.

19. The method of claim 17 wherein the defect is a cartilage defect.

20. The method of claim 13 wherein the mesenchymal stem cells are administered to enhance hematopoietic stem or progenitor cell engraftment in an individual in need thereof.

21. A method of treating a patient in need of mesenchymal stem cells, comprising administering human mesenchymal stem cells which bear fibroblast surface markers to said patient.

22. Isolated CD45+ human mesenchymal stem cells transfected with exogenous genetic material encoding a protein to be expressed.

* * * * *